(12) United States Patent
Schena et al.

(10) Patent No.: US 10,543,051 B2
(45) Date of Patent: Jan. 28, 2020

(54) METHOD FOR ENGAGING SURGICAL INSTRUMENT WITH TELEOPERATED ACTUATOR

(71) Applicant: Intuitive Surgical Operations, Inc., Sunnyvale, CA (US)

(72) Inventors: Bruce Michael Schena, Menlo Park, CA (US); Niels Smaby, Palo Alto, CA (US); Gregory W. Dachs, II, San Mateo, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 351 days.

(21) Appl. No.: 15/121,718

(22) PCT Filed: Mar. 17, 2015

(86) PCT No.: PCT/US2015/020880
§ 371 (c)(1),
(2) Date: Aug. 25, 2016

(87) PCT Pub. No.: WO2015/142788
PCT Pub. Date: Sep. 24, 2015

(65) Prior Publication Data
US 2016/0361126 A1 Dec. 15, 2016
US 2019/0274767 A2 Sep. 12, 2019

Related U.S. Application Data

(60) Provisional application No. 62/104,306, filed on Jan. 16, 2015, provisional application No. 62/103,991, (Continued)

(51) Int. Cl.
*A61B 34/35* (2016.01)
*A61B 34/37* (2016.01)
(Continued)

(52) U.S. Cl.
CPC ........ *A61B 46/10* (2016.02); *A61B 17/00234* (2013.01); *A61B 34/30* (2016.02);
(Continued)

(58) Field of Classification Search
CPC .......... B25J 19/0075; A61B 2090/0813; A61B 46/10
(Continued)

(56) References Cited

U.S. PATENT DOCUMENTS

| 4,542,272 A | * | 9/1985 | Hubbard | ................ H05B 6/101 219/641 |
|---|---|---|---|---|
| 5,214,573 A | | 5/1993 | Roza | |

(Continued)

FOREIGN PATENT DOCUMENTS

| CN | 1012972670 A | 10/2008 |
|---|---|---|
| CN | 101443162 A | 5/2009 |

(Continued)

OTHER PUBLICATIONS

International Search Report and Written Opinion for Application No. PCT/US15/21111, dated May 21, 2015, 10 pages.

(Continued)

*Primary Examiner* — Victor L MacArthur
*Assistant Examiner* — Gregory Robert Weber
(74) *Attorney, Agent, or Firm* — Haynes and Boone, LLP (57) ABSTRACT

A teleoperated surgical system has an instrument manipulator that includes a first carriage driver and a second carriage driver that each provide independent rotary motion. Each carriage driver includes a first engagement feature. A surgical instrument includes two instrument drivers that each receive the rotary motion from one of the two carriage drivers. Each instrument driver includes a second engagement feature that engages the first engagement feature to positively couple the carriage driver to the instrument driver.

(Continued)

The instrument drivers are rotationally coupled together. A manipulator controller controls rotation of the two carriage drivers and imparts a motion to the second carriage driver that is contrary to the rotation of the first carriage driver until the first engagement features positively engage the second engagement features. The surgical instrument may include an instrument shaft that can rotate indefinitely. The instrument drivers may be rotationally coupled to the instrument shaft.

21 Claims, 9 Drawing Sheets

Related U.S. Application Data filed on Jan. 15, 2015, provisional application No. 62/019,318, filed on Jun. 30, 2014, provisional application No. 61/954,557, filed on Mar. 17, 2014, provisional application No. 61/954,595, filed on Mar. 17, 2014, provisional application No. 61/954,571, filed on Mar. 17, 2014, provisional application No. 61/954,502, filed on Mar. 17, 2014, provisional application No. 61/954,497, filed on Mar. 17, 2014.

(51) Int. Cl.
| | | |
|---|---|---|
| *A61B 90/00* | (2016.01) | |
| *A61B 46/10* | (2016.01) | |
| *A61B 34/30* | (2016.01) | |
| *A61B 46/00* | (2016.01) | |
| *A61B 90/98* | (2016.01) | |
| *A61B 17/00* | (2006.01) | |
| *A61B 46/23* | (2016.01) | |
| *F16H 1/20* | (2006.01) | |

(52) U.S. Cl.
CPC .............. *A61B 34/35* (2016.02); *A61B 34/37* (2016.02); *A61B 46/40* (2016.02); *A61B 90/08* (2016.02); *A61B 90/361* (2016.02); *A61B 90/98* (2016.02); *A61B 46/23* (2016.02); *A61B 2017/00477* (2013.01); *A61B 2090/0813* (2016.02); *F16H 1/20* (2013.01); *Y10T 29/49817* (2015.01); *Y10T 403/59* (2015.01)

(58) Field of Classification Search
USPC ........................................................ 74/353
See application file for complete search history.

(56) References Cited

U.S. PATENT DOCUMENTS

| | | | |
|---|---|---|---|
| 5,679,423 | A | 10/1997 | Shah |
| 5,803,086 | A | 9/1998 | Scholz et al. |
| 6,331,181 | B1 | 12/2001 | Tierney et al. |
| 6,471,172 | B1 | 10/2002 | Lemke et al. |
| 7,096,870 | B2 | 8/2006 | Lamprich et al. |
| 7,125,403 | B2 | 10/2006 | Julian et al. |
| 7,758,569 | B2 | 7/2010 | Brock |
| 7,947,050 | B2 | 5/2011 | Lee et al. |
| 7,963,913 | B2 | 6/2011 | Devengenzo et al. |
| 8,220,468 | B2 | 7/2012 | Cooper et al. |
| 8,506,555 | B2 | 8/2013 | Ruiz |
| 8,529,582 | B2 | 9/2013 | Devengenzo et al. |
| 8,555,892 | B2 | 10/2013 | Traub |
| 9,687,312 | B2 | 6/2017 | Dachs, II et al. |
| 9,839,487 | B2 | 12/2017 | Dachs, II et al. |
| 1,002,219 | A1 | 7/2018 | Cooper et al. |
| 1,004,582 | A1 | 8/2018 | Dachs, II et al. |
| 10,213,268 | B2 | 2/2019 | Dachs, II et al. |
| 2002/0032452 | A1 | 3/2002 | Tierney et al. |
| 2002/0111635 | A1 | 8/2002 | Jensen et al. |
| 2003/0216723 | A1 | 11/2003 | Shinmura et al. |
| 2004/0049205 | A1 | 3/2004 | Lee et al. |
| 2005/0240178 | A1 | 10/2005 | Morley et al. |
| 2005/0244217 | A1 | 11/2005 | Burke et al. |
| 2006/0235436 | A1 | 10/2006 | Anderson et al. |
| 2006/0260622 | A1 | 11/2006 | Wooley et al. |
| 2007/0119274 | A1 | 5/2007 | Devengenzo et al. |
| 2007/0142971 | A1 | 6/2007 | Schena et al. |
| 2008/0103491 | A1 | 5/2008 | Omori et al. |
| 2008/0140088 | A1 | 6/2008 | Orban, III |
| 2010/0163057 | A1 | 7/2010 | Anderson et al. |
| 2010/0170519 | A1 | 7/2010 | Romo et al. |
| 2010/0175701 | A1 | 7/2010 | Reis et al. |
| 2010/0234857 | A1 | 9/2010 | Itkowitz et al. |
| 2011/0015650 | A1 | 1/2011 | Choi et al. |
| 2011/0084113 | A1 | 4/2011 | Bedi et al. |
| 2011/0118754 | A1 | 5/2011 | Dachs, II et al. |
| 2011/0213383 | A1 | 9/2011 | Lee et al. |
| 2011/0218551 | A1* | 9/2011 | Devengenzo .......... A61B 34/30 606/130 |
| 2011/0277776 | A1 | 11/2011 | McGrogan et al. |
| 2011/0288560 | A1 | 11/2011 | Shohat et al. |
| 2011/0290854 | A1 | 12/2011 | Timm et al. |
| 2011/0290855 | A1 | 12/2011 | Moore et al. |
| 2011/0295270 | A1 | 12/2011 | Giordano et al. |
| 2011/0313477 | A1 | 12/2011 | McLean et al. |
| 2012/0197094 | A1 | 8/2012 | Zhang et al. |
| 2012/0239060 | A1* | 9/2012 | Orban, III .............. A61B 34/30 606/130 |
| 2012/0247489 | A1 | 10/2012 | Orban, III et al. |
| 2012/0292367 | A1 | 11/2012 | Morgan et al. |
| 2013/0110129 | A1 | 5/2013 | Reid et al. |
| 2013/0211397 | A1* | 8/2013 | Parihar ................. A61B 18/18 606/33 |
| 2013/0211401 | A1 | 8/2013 | Bailey et al. |
| 2013/0274062 | A1* | 10/2013 | Arai ........................ F16H 61/12 477/5 |
| 2013/0274657 | A1* | 10/2013 | Zirps ................. A61M 25/0113 604/95.01 |
| 2013/0325034 | A1 | 12/2013 | Schena et al. |
| 2013/0331858 | A1 | 12/2013 | Devengenzo et al. |
| 2014/0001234 | A1* | 1/2014 | Shelton, IV ...... A61B 17/07207 227/176.1 |
| 2014/0066944 | A1 | 3/2014 | Taylor et al. |
| 2014/0069437 | A1 | 3/2014 | Reis et al. |
| 2015/0223832 | A1 | 8/2015 | Swaney et al. |
| 2015/0257841 | A1 | 9/2015 | Dachs, II |
| 2015/0257842 | A1 | 9/2015 | Dachs, II |
| 2016/0184037 | A1 | 6/2016 | Cooper et al. |
| 2016/0354173 | A1 | 12/2016 | Dachs, II et al. |
| 2016/0361049 | A1 | 12/2016 | Dachs, II et al. |
| 2016/0361124 | A1 | 12/2016 | Dachs, II et al. |
| 2016/0361127 | A1 | 12/2016 | Dachs, II et al. |
| 2016/0361129 | A1 | 12/2016 | Morrissette et al. |
| 2016/0361131 | A1 | 12/2016 | Dachs, II et al. |
| 2016/0367328 | A1 | 12/2016 | Dachs, II et al. |
| 2017/0172549 | A1 | 6/2017 | Smaby et al. |
| 2017/0273752 | A1 | 9/2017 | Dachs, II et al. |
| 2018/0064501 | A1 | 3/2018 | Dachs, II |
| 2018/0168752 | A1 | 6/2018 | Scheib et al. |
| 2018/0344419 | A1 | 12/2018 | Dachs, II et al. |

FOREIGN PATENT DOCUMENTS

| | | | |
|---|---|---|---|
| CN | 102630154 A | 8/2012 | |
| DE | 102012008535 A1 | 10/2013 | |
| DE | 102012013242 A1 | 1/2014 | |
| EP | 1862123 A2 | 12/2007 | |
| EP | 2259744 A1 | 12/2010 | |
| GB | 2538326 A | * 11/2016 | .......... B25J 19/0075 |
| JP | H0666326 A | 3/1994 | |
| KR | 20110032444 A | 3/2011 | |
| KR | 20110036452 A | 4/2011 | |
| KR | 20110095795 A | * 8/2011 | |
| KR | 20130080638 A | 7/2013 | |
| KR | 20130120316 A | 11/2013 | |
| WO | WO-2007075864 A1 | 7/2007 | |
| WO | WO-2007095637 A1 | 8/2007 | |

(56) References Cited

FOREIGN PATENT DOCUMENTS

| WO | WO-2007126443 A2 | 11/2007 |
|---|---|---|
| WO | WO-2009151205 A1 | 12/2009 |
| WO | WO-2010126128 A1 | 11/2010 |
| WO | WO-2011037394 A2 | 3/2011 |
| WO | WO-2011143016 A1 | 11/2011 |
| WO | WO-2013018931 A1 | 2/2013 |
| WO | WO-2013181536 A1 | 12/2013 |
| WO | WO-2014035803 A1 | 3/2014 |
| WO | WO-2015142824 A1 | 9/2015 |

OTHER PUBLICATIONS

International Search Report and Written Opinion for Application No. PCT/US15/20880, dated Jul. 14, 2015, 9 pages.
International Search Report and Written Opinion for Application No. PCT/US15/20882, dated May 29, 2015, 14 pages.
International Search Report and Written Opinion for Application No. PCT/US15/20884, dated Jun. 12, 2015, 13 pages.
International Search Report and Written Opinion for Application No. PCT/US15/20886, dated Jun. 4, 2015, 19 pages.
International Search Report and Written Opinion for Application No. PCT/US15/20876, dated Jun. 12, 2015, 17 pages.
International Search Report and Written Opinion for Application No. PCT/US15/20885, dated Jun. 5, 2015, 7 pages.
International Search Report and Written Opinion for Application No. PCT/US15/20888, dated Jun. 5, 2015, 9 pages.
International Search Report and Written Opinion for Application No. PCT/US15/21020, dated Jun. 5, 2015, 10 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. 15765493.0, dated Jul. 28, 2017, 7 pages.
Extended European Search Report for Application No. 15765779.2, dated Jul. 18, 2017, 8 pages.
Extended European Search Report for Application No. EP15764089.7, dated Oct. 25, 2017, 11 pages.
Extended European Search Report for Application No. EP15764268.7, dated Nov. 6, 2017, 8 pages.
Extended European Search Report for Application No. EP15764745.4, dated Oct. 30, 2017, 10 pages.
Extended European Search Report for Application No. EP15764940.1, dated Oct. 30, 2017, 8 pages.
Extended European Search Report for Application No. 15766019.2, dated Oct. 20, 2017, 7 pages.
Extended European Search Report for Application No. EP15764610.0, dated Nov. 23, 2017, 8 pages.
Extended European Search Report for Application No. EP15764881.7, dated Nov. 30, 2017, 10 pages.

* cited by examiner

FIG. 12 ized or destroyed in the steril-
METHOD FOR ENGAGING SURGICAL INSTRUMENT WITH TELEOPERATED ACTUATOR This application is a 371 of international application number PCT/US15/020880 filed Mar. 17, 2015, and claims benefit of the following earlier filed applications:

| U.S. | 61/954,497 | 17 Mar. 2014 (17-03-2014) |
| U.S. | 61/954,502 | 17 Mar. 2014 (17-03-2014) |
| U.S. | 61/954,557 | 17 Mar. 2014 (17-03-2014) |
| U.S. | 61/954,571 | 17 Mar. 2014 (17-03-2014) |
| U.S. | 61/954,595 | 17 Mar. 2014 (17-03-2014) |
| U.S. | 62/019,318 | 30 Jun. 2014 (30-06-2014) |
| U.S. | 62/103,991 | 15 Jan. 2015 (15-01-2015) |
| U.S. | 62/104,306 | 16 Jan. 2015 (16-01-2015) |

Each of these applications is specifically incorporated herein by reference to the greatest extent permitted.

FIELD

Embodiments of the invention relate to the field of mechanical couplers;

and more specifically, to couplers that provide a sterile barrier for coupling surgical instruments to teleoperated actuators.

BACKGROUND

Minimally invasive medical techniques have been used to reduce the amount of extraneous tissue which may be damaged during diagnostic or surgical procedures, thereby reducing patient recovery time, discomfort, and deleterious side effects. Traditional forms of minimally invasive surgery include endoscopy. One of the more common forms of endoscopy is laparoscopy, which is minimally invasive inspection or surgery within the abdominal cavity. In traditional laparoscopic surgery, a patient's abdominal cavity is insufflated with gas, and cannula sleeves are passed through small (approximately ½-inch) incisions in the musculature of the patient's abdomen to provide entry ports through which laparoscopic surgical instruments can be passed in a sealed fashion.

The laparoscopic surgical instruments generally include a laparoscope for viewing the surgical field and surgical instruments having end effectors such as surgical tools. Typical surgical tools include clamps, graspers, scissors, staplers, and needle holders, for example. The surgical instruments are similar to those used in conventional (open) surgery, except that the end effector of each surgical instrument is separated from its handle by an approximately 12-inch long extension tube, for example, so as to permit the operator to introduce the end effector to the surgical site and to control movement of the end effector relative to the surgical site from outside a patient's body.

In order to provide improved control of the end effector, it may be desirable to control the surgical instrument with teleoperated actuators. The surgeon may operate controls on a console to indirectly manipulate the instrument that is connected to the teleoperated actuators. The surgical instrument is detachably coupled to the teleoperated actuators so that the surgical instrument can be separately sterilized and selected for use as needed instrument for the surgical procedure to be performed. The surgical instrument may be changed during the course of a surgery.

Performing surgery with teleoperated surgical instruments creates new challenges. One challenge is the need to maintain the region adjacent the patient in a sterile condition. However, the motors, sensors, encoders and electrical connections that are necessary to control the surgical instruments typically cannot be sterilized using conventional methods, e.g., steam, heat and pressure or chemicals, because they would be damaged or destroyed in the sterilization process.

Another challenge with teleoperated surgery systems is that a surgeon will typically employ several different surgical instruments during a procedure. A number of different surgical instruments will typically be introduced through the same trocar sleeve during the operation to limit the number of incisions required. Thus, there are a limited number of instrument manipulators available, often fewer than the number of surgical instruments used during a procedure. Therefore the surgical instruments may be attached and detached from the same instrument holder a number of times during an operation.

It would be desirable to provide an easier and more effective way to engage a surgical instrument with a teleoperated actuator drive while preventing contamination of the teleoperated actuator and allowing quick and reliable engagement of the mechanical couplers that transfer motion from the teleoperated actuator drive to the surgical instrument through a sterile barrier.

SUMMARY

A teleoperated surgical system has an instrument manipulator that includes a first carriage driver and a second carriage driver that each provide independent rotary motion. Each carriage driver includes a first engagement feature. A surgical instrument includes two instrument drivers that each receive the rotary motion from one of the two carriage drivers. Each instrument driver includes a second engagement feature that engages the first engagement feature to positively couple the carriage driver to the instrument driver. The instrument drivers are rotationally coupled together. A manipulator controller controls rotation of the two carriage drivers and imparts a motion to the second carriage driver that is contrary to the rotation of the first carriage driver until the first engagement features positively engage the second engagement features. The surgical instrument may include an instrument shaft that can rotate indefinitely. The instrument drivers may be rotationally coupled to the instrument shaft.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements.

The invention may best be understood by referring to the following description and accompanying drawings that are used to illustrate embodiments of the invention by way of example and not limitation. In the drawings, in which like reference numerals indicate similar elements.

DESCRIPTION OF EMBODIMENTS

In the following description, numerous specific details are set forth. However, it is understood that embodiments of the invention may be practiced without these specific details. In other instances, well-known circuits, structures, and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

Terminology

The terminology used herein is for the purpose of describing particular embodiments only and is not intended to be limiting of the invention. Spatially relative terms, such as "beneath," "below," "lower," "above," "upper," and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a," "an," and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The term "object" generally refers to a component or group of components. For example, an object may refer to either a pocket or a boss of a disk within the specification or claims. Throughout the specification and claims, the terms "object," "component," "portion," "part," and "piece" are used interchangeably.

The terms "instrument" and "surgical instrument" are used herein to describe a medical device configured to be inserted into a patient's body and used to carry out surgical or diagnostic procedures. The instrument includes an end effector. The end effector may be a surgical tool associated with one or more surgical tasks, such as a forceps, a needle driver, a shears, a bipolar cauterizer, a tissue stabilizer or retractor, a clip applier, an anastomosis device, an imaging device (e.g., an endoscope or ultrasound probe), and the like. Some instruments used with embodiments of the invention further provide an articulated support (sometimes referred to as a "wrist") for the surgical tool so that the position and orientation of the surgical tool can be manipulated with one or more mechanical degrees of freedom in relation to the instrument's shaft. Further, many surgical end effectors include a functional mechanical degree of freedom, such as jaws that open or close, or a knife that translates along a path. Surgical instruments may also contain stored (e.g., on a semiconductor memory inside the instrument) information that may be permanent or may be updatable by the surgical system. Accordingly, the system may provide for either one-way or two-way information communication between the instrument and one or more system components.

The term "pocket" may be construed broadly as a recess of a workspace which is configured such that a protrusion is able to engage the pocket. Such a coupling process occurs when a protrusion of the appropriate shape and size is inserted into the pocket.

The term "boss" may be construed broadly as an extending or protruding feature on a workspace. A boss may be configured as any shape or size. One use of a boss is to participate in a coupling process with a pocket through insertion of the boss into the pocket. Throughout the specification, the terms "boss" and "protrusion" are used interchangeably.

The term "engagement feature" may be construed broadly as a "pocket" or a "boss" or any piece used to couple two or more objects.

The term "positively coupled" may be construed broadly as any event in which two or more objects are connected in a manner allowing the positively coupled objects to operate in conjunction with one another such that there is no relative movement between the objects. It should be noted that positive coupling does not require a direct connection (e.g., direct physical or electrical connection) but that a multiplicity of objects or components may be used to positively couple two or more objects. For example, objects A and B may be positively coupled through the use of object C. As another example, objects D and E may be positively coupled when object D, a protrusion, is received into the recess of object E, a pocket. Throughout the specification and claims, the terms "couple," "connect" or "engage" are used interchangeably.

The term "coupler" may be construed generally as a first component that couples a second component to a third component.

The term "rotary receptacle" may be construed as a receiving point for an input. For example, a rotary receptacle may be a component that receives an input from a motor causing the motor to remain stationary or rotate in a particular direction. The term "rotary input" may refer to such an input from a motor.

In addition, the term "detachably coupled" may be construed to mean a coupling event between two or more objects that is not permanent. This means that objects that are detachably coupled may be uncoupled and separated such that they no longer operate in conjunction.

Lastly, the terms "or" and "and/or" as used herein are to be interpreted as inclusive or meaning any one or any combination. Therefore, "A, B or C" or "A, B and/or C" mean "any of the following: A; B; C; A and B; A and C; B and C; A, B, and C." An exception to this definition will occur only when a combination of elements, functions, steps or acts are in some way inherently mutually exclusive.

Overview of a Functional Teleoperated Surgical System

Figure 1:
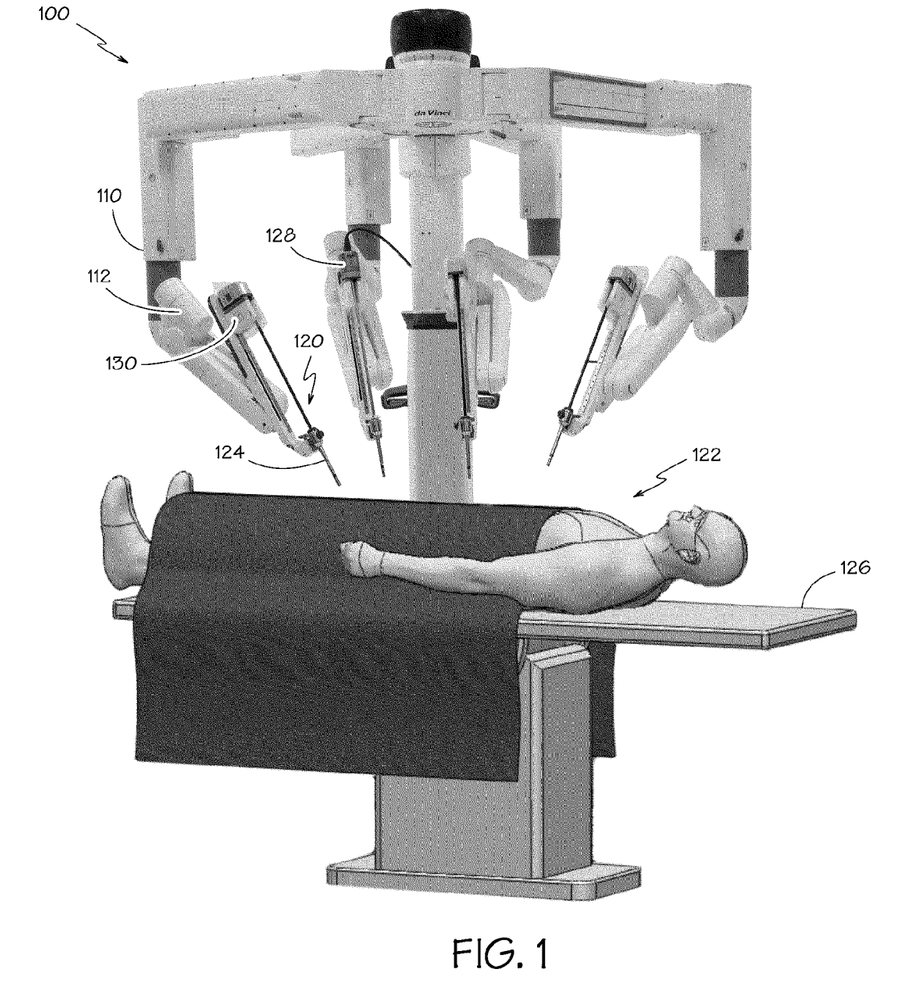
FIG. 1 is a view of an illustrative patient-side portion of a teleoperated surgical system.

FIG. 1 is a view of an illustrative patient-side portion 100 of a teleoperated surgical system, in accordance with embodiments of the present invention. The patient-side portion 100 includes support assemblies 110 and one or more surgical instrument manipulators 112 at the end of each support assembly. The support assemblies optionally include one or more unpowered, lockable setup joints that are used to position the surgical instrument manipulator(s) 112 with reference to the patient for surgery. As depicted, the patient-side portion 100 rests on the floor. In other embodiments the patient-side portion may be mounted to a wall, to the ceiling, to the operating table 126, which also supports the patient's body 122, or to other operating room equipment. Further, while the patient-side portion 100 is shown as including four surgical instrument manipulators 112, more or fewer surgical instrument manipulators 112 may be used. Still further, the patient-side portion 100 may consist of a single assembly as shown, or it may include two or more separate assemblies, each optionally mounted in various possible ways.

Each surgical instrument manipulator 112 supports one or more surgical instruments 120 that operate at a surgical site within the patient's body 122. Each surgical instrument manipulator 112 may be provided in a variety of forms that allow the associated surgical instrument to move with one or more mechanical degrees of freedom (e.g., all six Cartesian degrees of freedom, five or fewer Cartesian degrees of freedom, etc.). Typically, mechanical or control constraints restrict each surgical instrument manipulator 112 to move its associated surgical instrument around a center of motion on the surgical instrument that stays stationary with reference to the patient, and this center of motion is typically located to be at the position where the surgical instrument enters the body.

A functional teleoperated surgical system will generally include a vision system portion (not shown) that enables the operator to view the surgical site from outside the patient's body 122. The vision system typically includes a surgical instrument that has a video-image-capture function 128 (a "camera instrument") and one or more video displays for displaying the captured images. In some surgical system configurations, the camera instrument 128 includes optics that transfer the images from the distal end of the camera instrument 128 to one or more imaging sensors (e.g., CCD or CMOS sensors) outside of the patient's body 122. Alternatively, the imaging sensor(s) may be positioned at the distal end of the camera instrument 128, and the signals produced by the sensor(s) may be transmitted along a lead or wirelessly for processing and display on the video display. An illustrative video display is the stereoscopic display on the surgeon's console in surgical systems commercialized by Intuitive Surgical, Inc., Sunnyvale, Calif.

A functional teleoperated surgical system will further include a control system portion (not shown) for controlling the movement of the surgical instruments 120 while the instruments are inside the patient. The control system portion may be at a single location in the surgical system, or it may be distributed at two or more locations in the system (e.g., control system portion components may be in the system's patient-side portion 100, in a dedicated system control console, or in a separate equipment rack). The teleoperated master/slave control may be done in a variety of ways, depending on the degree of control desired, the size of the surgical assembly being controlled, and other factors. In some embodiments, the control system portion includes one or more manually-operated input devices, such as a joystick, exoskeletal glove, a powered and gravity-compensated manipulator, or the like. These input devices control teleoperated motors which, in turn, control the movement of the surgical instrument.

The forces generated by the teleoperated motors are transferred via drivetrain mechanisms, which transmit the forces from the teleoperated motors to the surgical instrument 120. In some telesurgical embodiments, the input devices that control the manipulator(s) may be provided at a location remote from the patient, either inside or outside the room in which the patient is placed. The input signals from the input devices are then transmitted to the control system portion. Persons familiar with telemanipulative, teleoperative, and telepresence surgery will know of such systems and their components, such as the da Vinci® Surgical System commercialized by Intuitive Surgical, Inc. and the Zeus® Surgical System originally manufactured by Computer Motion, Inc., and various illustrative components of such systems.

As shown, both the surgical instrument 120 and an optional entry guide 124 (e.g., a cannula in the patient's abdomen) are removably coupled to the distal end of a manipulator 112, with the surgical instrument 120 inserted through the entry guide 124. Teleoperated actuators in the manipulator 112 move the surgical instrument 120 as a whole. The manipulator 112 further includes an instrument carriage 130. The surgical instrument 120 is detachably connected to the carriage 130. The teleoperated actuators housed in the carriage 130 provide a number of controller motions which the surgical instrument 120 translates into a variety of movements of the end effector on the surgical instrument. Thus the teleoperated actuators in the carriage 130 move only one or more components of the surgical instrument 120 rather than the instrument as a whole. Inputs to control either the instrument as a whole or the instrument's components are such that the input provided by a surgeon to the control system portion (a "master" command) is translated into a corresponding action by the surgical instrument (a "slave" response).

Figure 2:
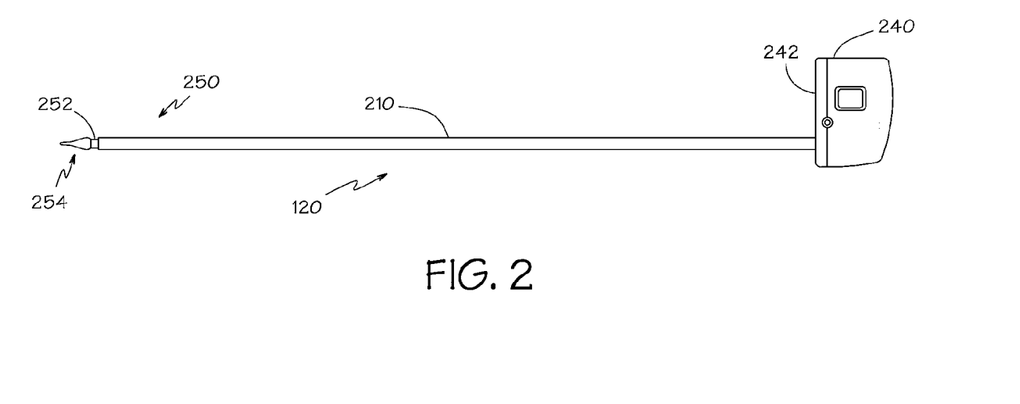
FIG. 2 is a side view of a surgical instrument for use with a teleoperated actuator.

FIG. 2 is a side view of an illustrative embodiment of the surgical instrument 120, comprising a distal portion 250 and a proximal control mechanism 240 coupled by an elongate tube 210. The distal portion 250 of the surgical instrument 120 may provide any of a variety of surgical tools, such as the forceps 254 shown, a needle driver, a cautery device, a cutting tool, an imaging device (e.g., an endoscope or ultrasound probe), or a combined device that includes a combination of two or more various tools and imaging devices. In the embodiment shown, the surgical tool 254 is coupled to the elongate tube 210 by a "wrist" 252 that allows the orientation of the surgical tool to be manipulated with reference to the instrument tube 210.

Surgical instruments that are used with the invention may control their end effectors (surgical tools) with a plurality of rods and/or flexible cables. Rods, which may be in the form of tubes, may be combined with cables to provide a "push/pull" control of the end effector with the cables providing flexible sections as required. A typical elongate tube 210 for a surgical instrument 120 is small, perhaps five to eight millimeters in diameter, roughly the diameter of a large soda straw. The diminutive scale of the mechanisms in the surgical instrument 120 creates unique mechanical conditions and issues with the construction of these mechanisms that are unlike those found in similar mechanisms constructed at a larger scale, because forces and strengths of materials do not scale at the same rate as the size of the mechanisms. The cables must fit within the elongate tube 210 and be able to bend as they pass through the wrist joint 252.

In order to provide a sterile operation area while using a functional teleoperated surgical system, it is preferred that a barrier be placed between the non-sterile system and the sterile surgical field. Therefore, a sterile component, such as an instrument sterile adapter (ISA), is placed between the surgical instrument 120 and the teleoperated surgical instrument manipulator 112. The placement of an instrument sterile adapter between the surgical instrument 120 and the surgical instrument manipulator 112 includes the benefit of ensuring a sterile coupling point for the surgical instrument 120 and the surgical instrument manipulator 112. This permits removal of surgical instruments from the surgical instrument manipulator 112 and exchange with other surgical instruments during the course of a surgery.

Figure 3A:
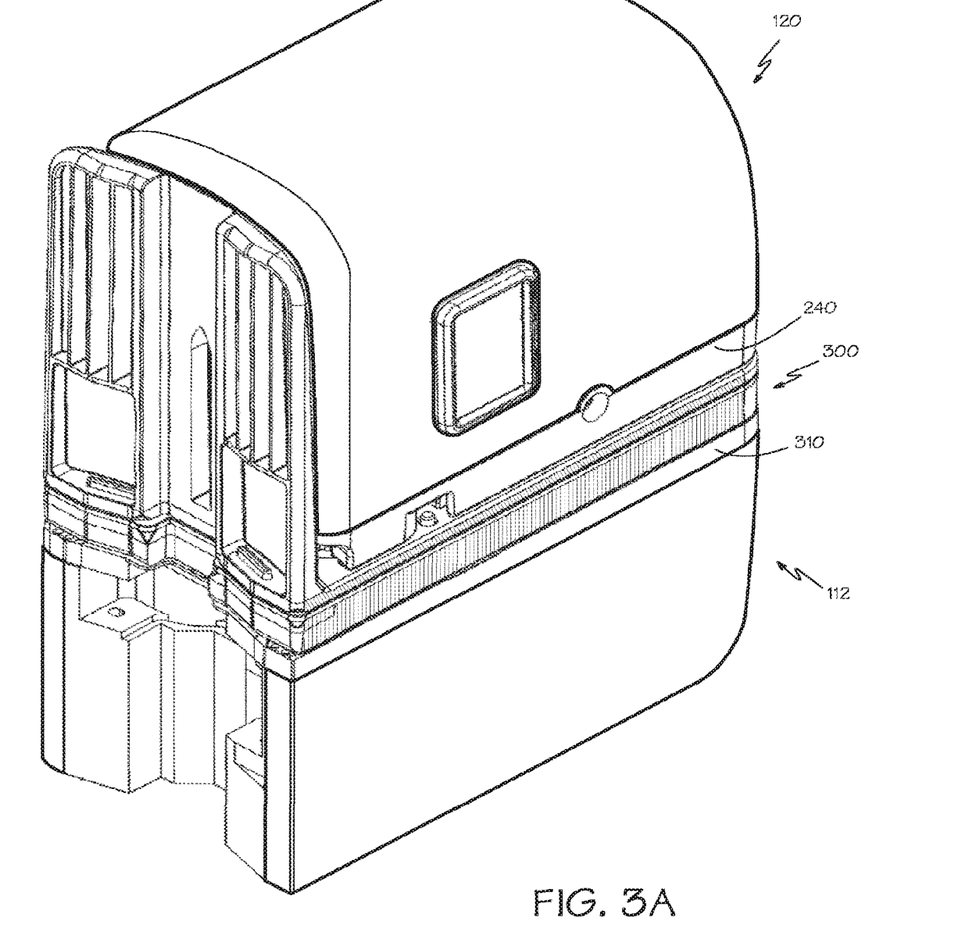
FIG. 3A is an illustration of an exemplary embodiment of a coupling of a surgical instrument, a carriage of a surgical instrument manipulator, and an instrument sterile adapter (ISA).

FIG. 3A shows a portion of an exemplary embodiment of a proximal control mechanism 240 of a surgical instrument 120, a carriage 310 (e.g., instrument carriage 130) of a teleoperated surgical instrument manipulator 112, and an instrument sterile adapter (ISA) 300 in a coupled condition.

Figure 3B:
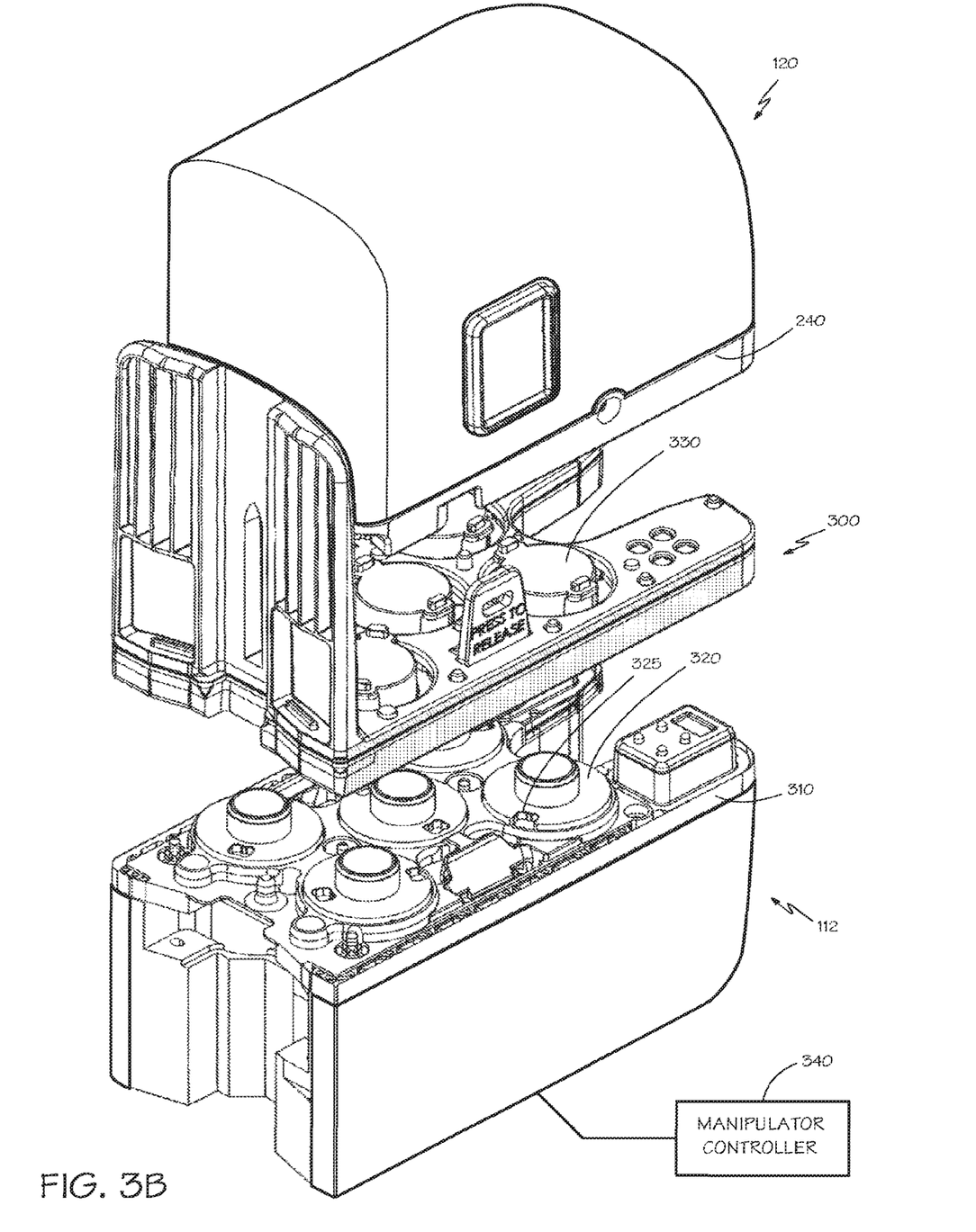
FIG. 3B is an illustration of an exemplary embodiment of the coupler system of FIG. 3A.

FIG. 3B shows an exploded view of the coupler system of FIG. 3A. In one embodiment, the first stage of the coupling process includes the ISA 300 coupling with the carriage 310. Carriage drivers 320 on the carriage 310 are rotated to cause engagement features 325 on the drivers to mate with reciprocal features (not shown) on the corresponding ISA couplers 330. The carriage drivers 320 may each be rotated by an electric motor that receives control signals from a manipulator controller 340. The manipulator controller 340 may provide control signals that allow each carriage driver 320 to be controlled independently of the remaining carriage drivers. The surgical instrument 120 is coupled with the ISA 300. The ISA couplers 330 are rotated by the carriage drivers 320 to engage corresponding instrument drivers (not shown).

It is important to ensure that the surgical instrument 120 properly engages the surgical instrument manipulator 112 through the ISA 300. The carriage drivers 320 need to positively couple with the ISA couplers 330. The ISA couplers 330 in turn need to positively couple with the instrument drivers.

Figure 4:
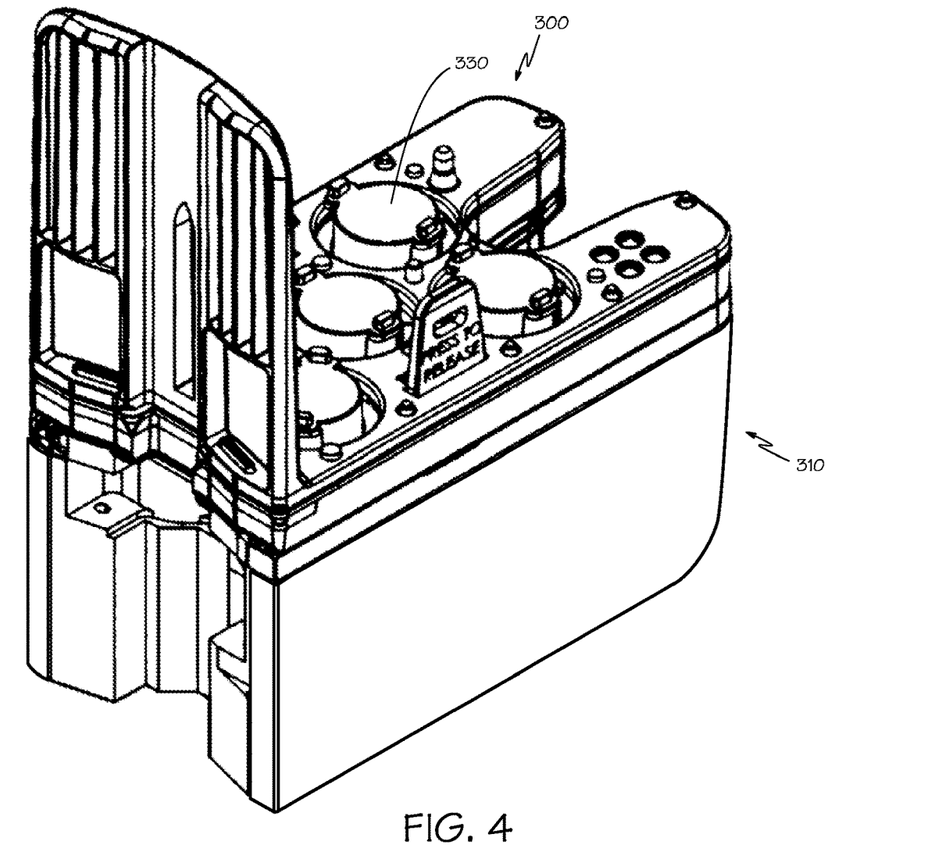
FIG. 4 is an illustration of an exemplary embodiment of an assembled ISA coupled to a carriage.

FIG. 4 is an illustration of an exemplary embodiment of an assembled ISA 300 coupled to a carriage 310. The ISA 300 includes a plurality of ISA couplers 330. The embodiment of FIG. 4 illustrates the ISA 300 including five ISA couplers 330. The number of ISA couplers 330 is not limited to five, but may be greater than or less than five. With reference to FIG. 3B, the ISA couplers 330 are in turn coupled to carriage drivers 320 and motors housed within the carriage 310. When the ISA couplers are coupled to carriage drivers and engaged, the ISA presents a sterile surface for coupling surgical instruments that is equivalent to the surface of the carriage.

Figure 5:
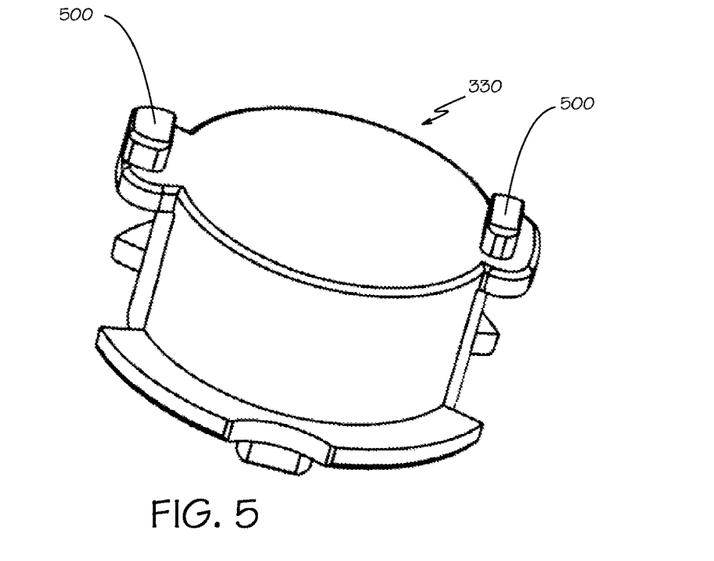
FIG. 5 is an illustration of an exemplary embodiment of an ISA coupler.

FIG. 5 shows an exemplary embodiment of an ISA coupler 330. The ISA coupler 330 includes two ISA engagement features 500. It should be noted that the number of engagement features are variable.

Instrument Engagement

Figure 6:
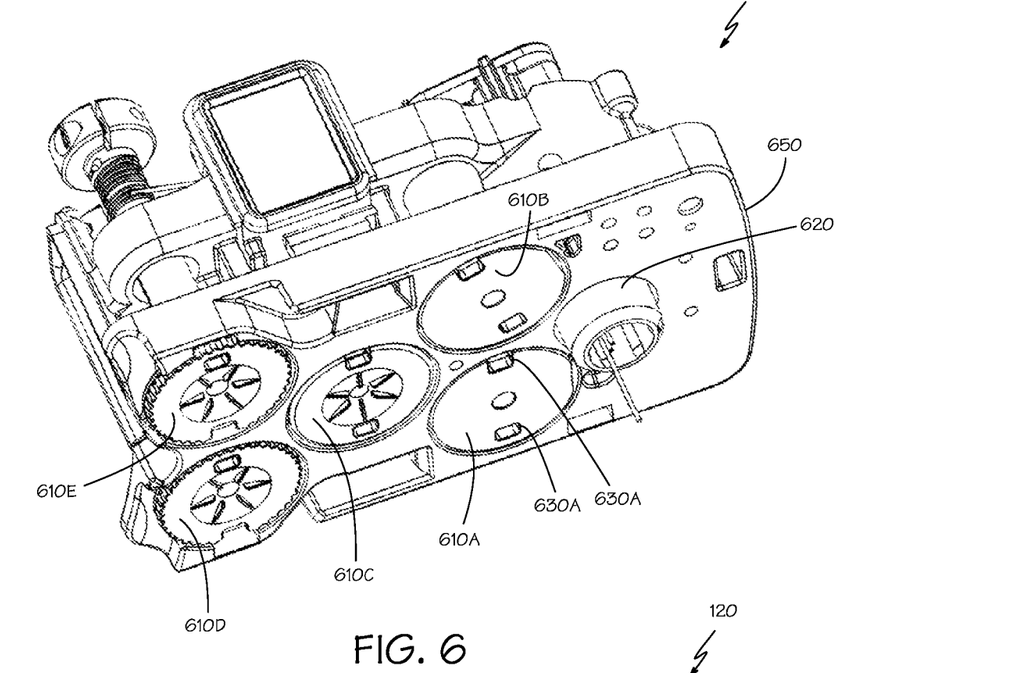
FIG. 6 is an illustration of an exemplary embodiment of the underside of a portion of a surgical instrument.

FIG. 6 is an exemplary illustration of the underside of a portion of a surgical instrument 120. In the embodiment, the surgical instrument 120 is shown to include a plurality of instrument drivers 610A-610E, an instrument shaft coupler 620 and a bottom plate 650. The instrument shaft coupler 620 engages the elongate tube 210 seen in FIG. 1. In the embodiment, five instrument drivers 610A-610E are shown. However, the number of instrument drivers is not limited to five; other embodiments may contain greater than or less than five. Furthermore, the placement of the instrument drivers is not limited to the configuration illustrated in FIG. 6. Two or more of the instrument drivers may be rotationally coupled so that two or more motors may be used to drive a single function of the surgical instrument. When two or more instrument drivers are rotationally coupled, rotation of either instrument driver can cause the other instrument drivers to rotate.

Figure 7:
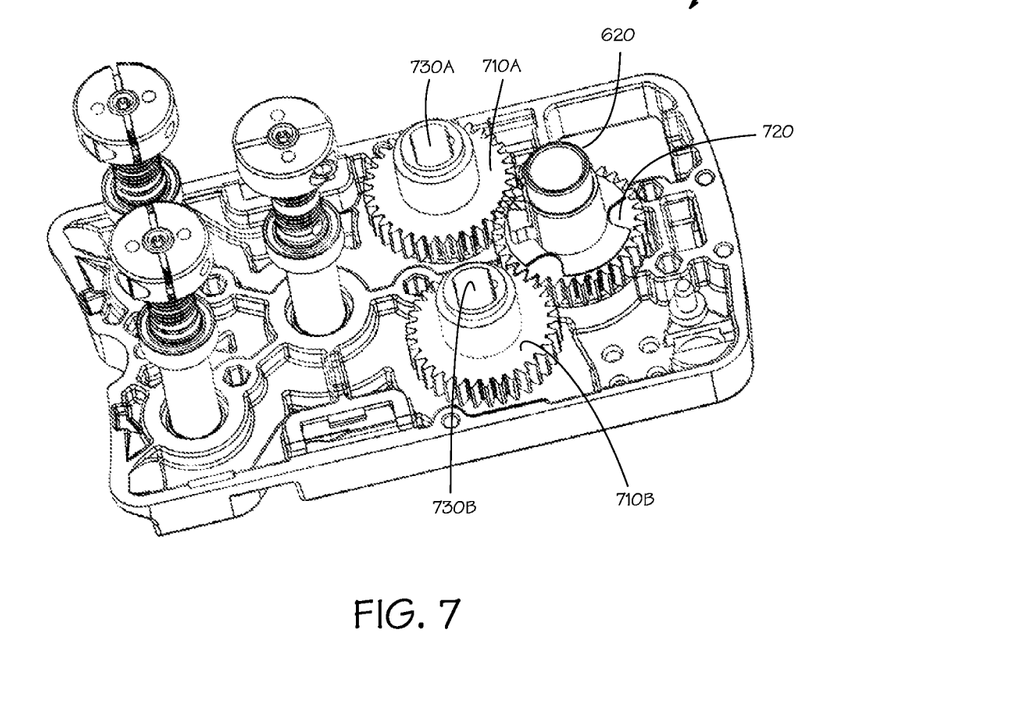
FIG. 7 is an illustration of an exemplary embodiment of the upper side of the surgical instrument shown in FIG. 6 with some components removed for clarity.

FIG. 7 is an exemplary illustration of the upper side of the surgical instrument 120 shown in FIG. 6 with some components not shown for ease of explanation. A first keyed instrument driver shaft 730A extends from the first instrument driver 610A and a second keyed instrument driver shaft 730B extends from the second instrument driver 610B. The keyed shafts extend through the bottom plate 650 of the surgical instrument and engage a first instrument driver gear 710A and a second instrument driver gear 710B.

In the embodiment shown in FIG. 7, the instrument shaft coupler 620 extends through the bottom plate 650 of the surgical instrument and engages an instrument shaft gear 720. Rotating the instrument shaft gear 720 rotates the elongate tube 210 seen in FIG. 1. The first instrument driver gear 710A and the second instrument driver gear 710B each engage the instrument shaft gear 720. Thus rotating either of the first instrument driver 610A or the second instrument driver 610B will rotate the instrument shaft gear and the coupled elongate tube 210 seen in FIG. 1. Of course, both the first instrument driver 610A and the second instrument driver 610B can be rotated cooperatively to apply a greater rotational force to the elongate tube 210.

The first instrument driver 610A and the second instrument driver 610B are rotationally coupled by the gear train that includes the first and second instrument driver gears 710A, 710B and the instrument shaft gear 720. This is merely one example of a way that two or more instrument drivers can be rotationally coupled. Other arrangements for rotationally coupling instrument drivers are possible, such as belt drives, chain and sprocket drives, and other arrangements of gear drives. The rotational coupling of the instrument drivers may include additional components such as a torque limiting slip clutch or a one-way clutch that couples rotation of the instrument drivers when driven in one direction but allows them to rotate independently in the opposite direction.

In the rotational coupling arrangement seen in FIG. 7, the first instrument driver 610A and the second instrument driver 610B rotate in one direction while the instrument shaft coupler 620 rotates in the opposite direction. For example, if the first instrument driver 610A and the second instrument driver 610B rotate clockwise, the instrument shaft coupler 620 will rotate counter-clockwise. In other arrangements, the first instrument driver 610A and the second instrument driver 610B may be rotationally coupled to rotate in opposite directions and/or with rotational speed ratios other than 1:1.

If the ISA engagement features 500 and the instrument engagement features 630 are not initially in alignment when an attempt to couple the surgical instrument 120 with the ISA 300 is made, the ISA engagement features 500 will come into contact with a disk portion of the instrument driver 610. Each carriage driver 320 may contain a spring-loaded mechanism such that when a force is applied to the carriage driver 320, the carriage driver 320 recedes into the carriage 310. When the ISA engagement features 500 are not in alignment with the instrument engagement features 630, the ISA coupler 330 will be displaced axially toward the carriage causing the carriage driver 320 to recede into the carriage 310. In other embodiments, the ISA coupler 330 or the instrument driver 610 may include a spring-loaded mechanism in addition to or as an alternative to the spring-loaded mechanism of the carriage driver 320 to allow axial displacement of the drivers and/or couplers prior to engagement of these components.

To engage a surgical instrument 120 with the ISA 300, the ISA couplers 330 are rotated in order to align the ISA engagement features 500 with the instrument engagement features 630. However, due to friction that is created when the ISA engagement features 500 come into contact with the disk portion of the instrument driver 610, the instrument drivers 610 may rotate as the ISA couplers 330 turn. It is necessary to ensure that the instrument engagement features 630 positively engage the ISA engagement features 500 so that a surgical instrument attached to the ISA 300 can be properly controlled.

Instrument drivers that are coupled to functions that have a limited range, such as an end effector wrist, have a corresponding limited rotational range with a hard-stop at the end of the range. Therefore, when rotating the ISA coupler to engage an instrument driver that has a hard-stop, it is assured that the instrument driver must eventually stop turning which ensures that the ISA coupler can be rotated into engagement with the instrument driver. However, when the instrument driver does not provide a hard-stop, such as rotation of a camera, simply rotating the ISA coupler will not ensure proper engagement with the instrument driver.

The configuration of the instrument shaft coupler 620 and the two rotationally coupled instrument drivers 610A, 610B may not provide a hard-stop. If the instrument shaft coupler 620 does not include a hard-stop, the instrument shaft coupler 620 and, due to the gear coupling, both instrument drivers 610, may rotate indefinitely. If the instrument drivers 610 rotate indefinitely, they may never properly engage with the ISA couplers 330.

Therefore, there is a need for a way to ensure that the friction caused by the ISA engagement features 500 coming in contact with the disk portions of the instrument drivers 610 of a surgical instrument 120 does not prevent a proper engagement between the ISA engagement features 500 and the instrument engagement features 630 for functions that do not provide a hard-stop.

Figure 8:
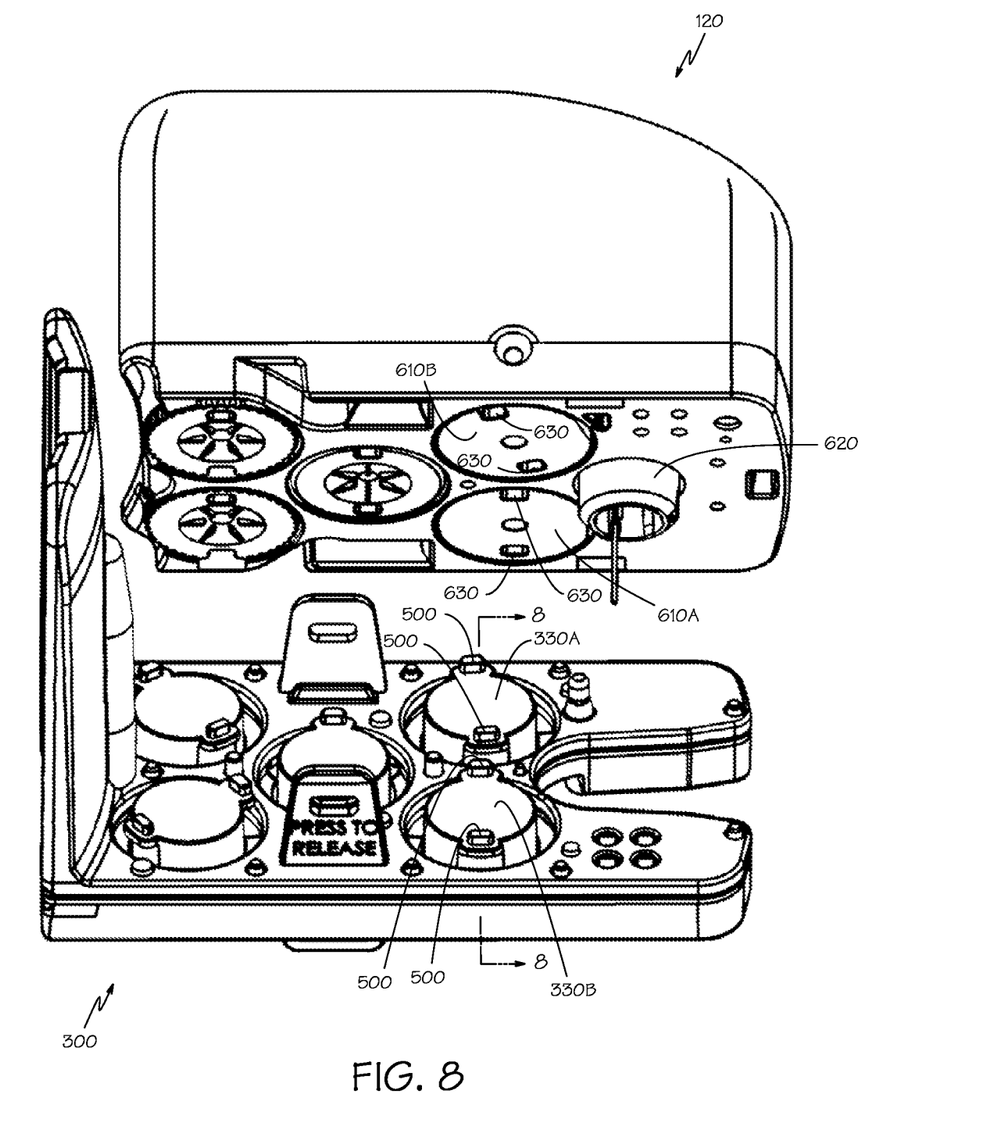
FIG. 8 is an illustration of an exemplary embodiment of the coupler system of an ISA and a surgical instrument.

FIG. 8 illustrates an exemplary embodiment of the coupler system of an ISA 300 and a surgical instrument 120 in which two rotationally coupled instrument drivers 610A, 610B do not provide a hard-stop. The ISA engagement features 500 will come in contact with the disk portions of two rotationally coupled instrument drivers 610. Rotating the ISA couplers 330 may cause the corresponding instrument drivers 610 to rotate due to the friction between the engagement features and the disk surfaces. This may hinder positively engaging the ISA couplers 330 with the corresponding instrument drivers 610 with the engagement features.

FIGS. 9 through 12 are cross-sectional views of the exemplary embodiment of the coupler system of an ISA 300 and a surgical instrument 120 taken along section line 8-8 in FIG. 8. The cross-sectional views show portions of the surgical instrument 120, the ISA 300, and the carriage 310 to illustrate the process of positively engaging the ISA couplers 330 with the corresponding instrument drivers 610

Figure 9:
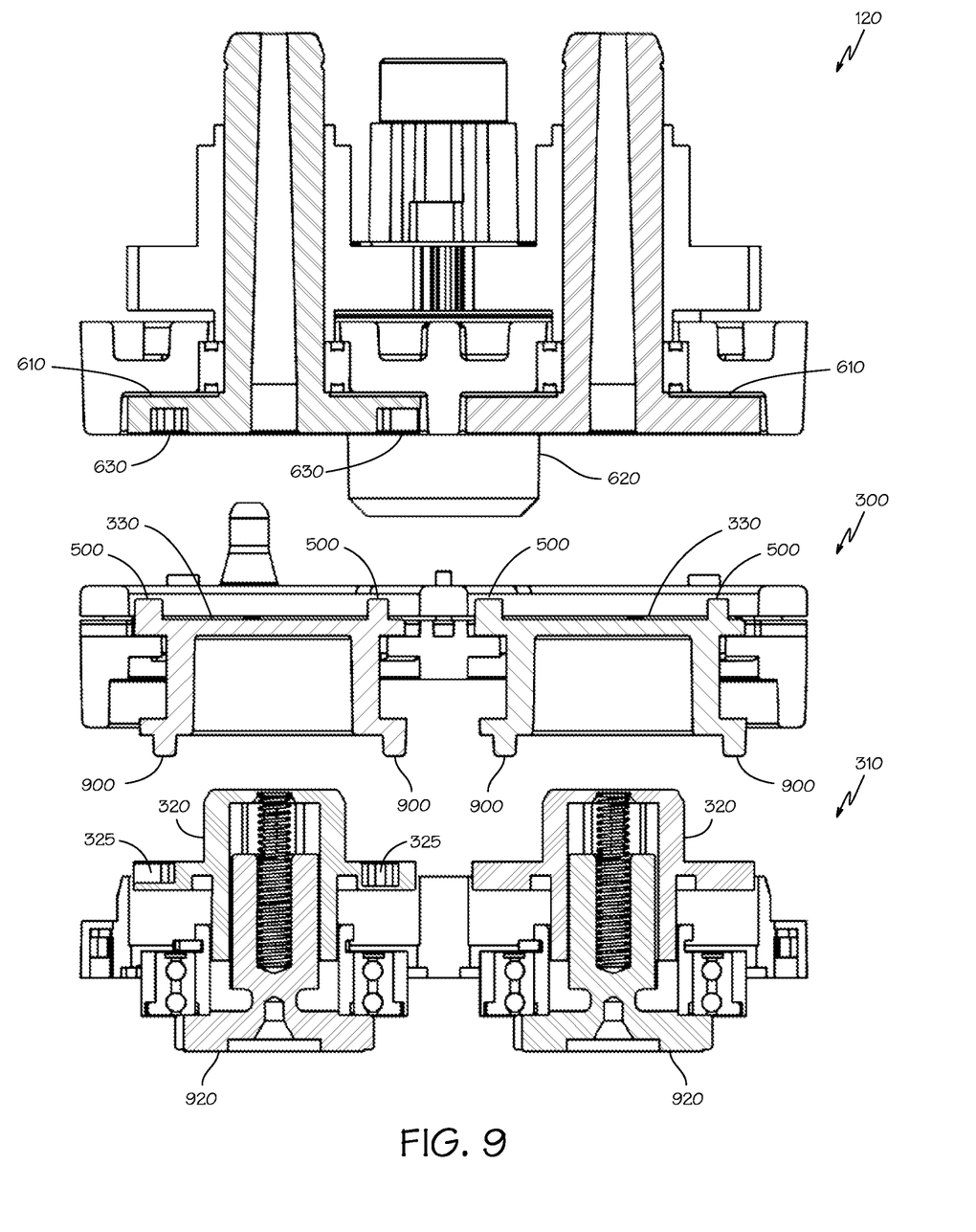
FIG. 9 is an illustration of an exemplary embodiment of a surgical instrument, an ISA, and a carriage separated from one another.

FIG. 9 shows the surgical instrument 120, the ISA 300, and the carriage 310 separated from one another. The carriage 310 includes spring loaded carriage drivers 320 having engagement features 325 that mate with reciprocal features 900 on the corresponding ISA couplers 330. Likewise, the ISA 300 includes ISA couplers 330 that can move axially within the ISA, the ISA couplers having ISA engagement features 500 that mate with instrument engagement features 630 on the instrument driver 610 of the surgical instrument 120.

Figure 10:
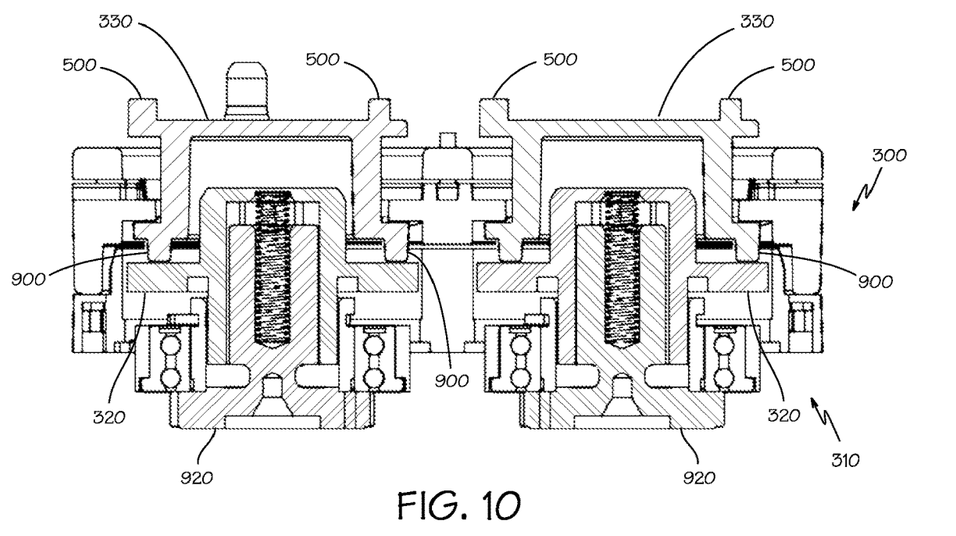
FIG. 10 is an illustration of an ISA and a carriage latched together.

FIG. 10 shows the ISA 300 and the carriage 310 latched together with the engagement features on the carriage drivers 320 not mated with the reciprocal features 900 on the corresponding ISA couplers 330. The spring loaded carriage drivers 320 are moved axially by the reciprocal features 900 on the ISA couplers 330 when the driver has not engaged the coupler.

Figure 11:
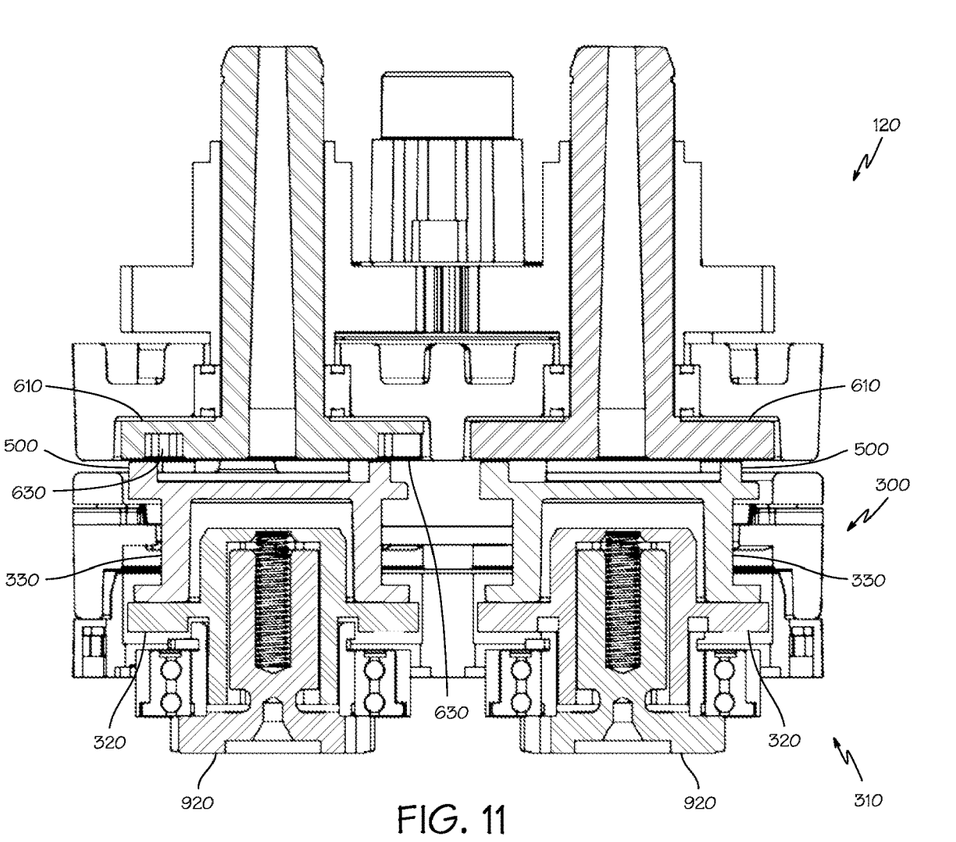
FIG. 11 is an illustration of an ISA and a carriage latched together.

FIG. 11 shows the ISA 300 and the carriage 310 latched together with the engagement features on the carriage drivers mated with the reciprocal features on the corresponding ISA couplers 330. The surgical instrument 120 and the ISA 300 are latched together with the instrument engagement features 630 on the instrument drivers 610 not mated with the ISA engagement features 500 on the corresponding ISA couplers 330. The spring loaded carriage drivers 320 are moved axially by the axial movement of the ISA couplers 330 when the instrument driver 610 has not engaged the ISA coupler 330.

Figure 12:
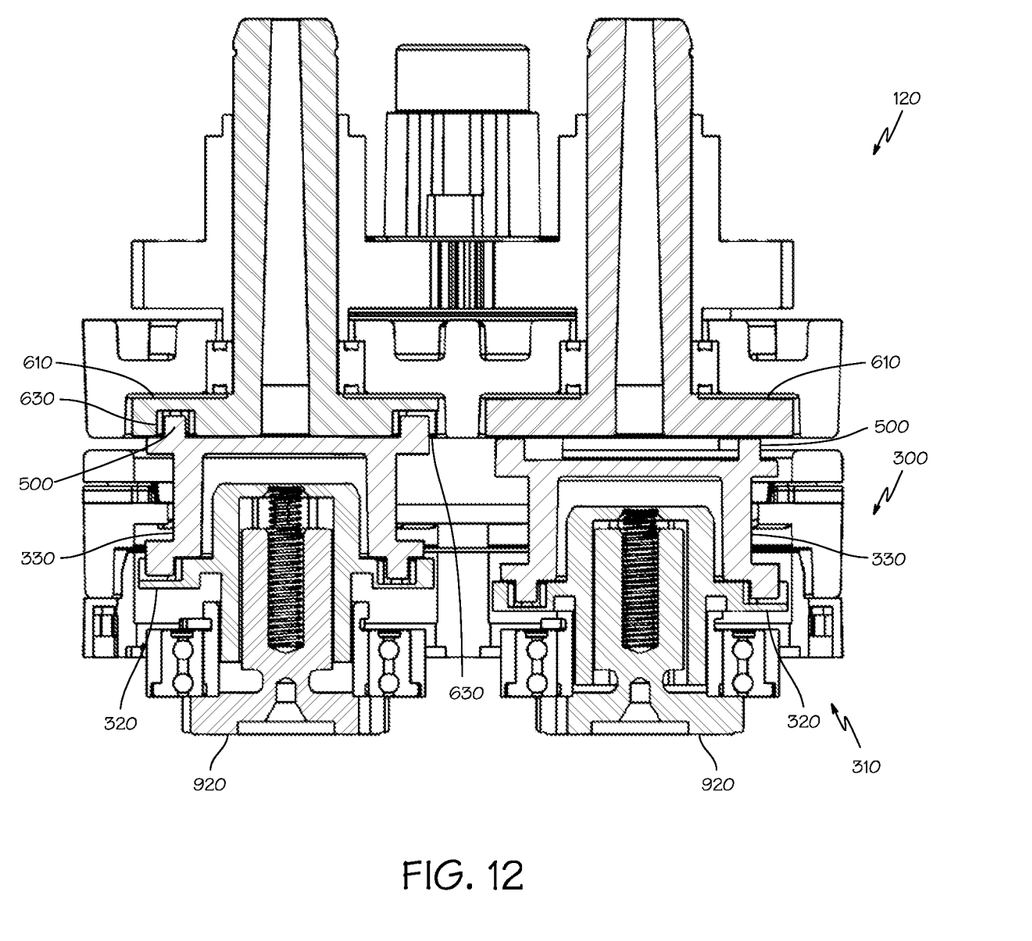
FIG. 12 is an illustration of a surgical instrument, an ISA, and a carriage latched together.

FIG. 12 shows the surgical instrument 120, the ISA 300, and the carriage 310 latched together. The left instrument driver 610 has engaged the ISA coupler 330. This engagement allows the left spring loaded carriage driver 320 to move axially toward the ISA 300 and the surgical instrument 120.

A method to couple a surgical instrument with an instrument manipulator when two rotationally coupled instrument drivers of the surgical instrument do not include a hard-stop takes advantage of the rotational coupling of the instrument drivers. Rotary motion of the carriage drivers is frictionally coupled to corresponding instrument drivers. While the engagement features of the carriage drivers have not positively engaged the engagement features on the corresponding instrument drivers, a first carriage driver is rotated. A motion is imparted to a second carriage driver that is contrary to the rotation of the first carriage driver until second engagement features coupled to each of the carriage drivers positively engage the first engagement features on the corresponding instrument drivers. "Motion of the second carriage driver contrary to the rotation of the first carriage driver" is used to mean that the motion of the second carriage driver is something other than the motion that would allow the second carriage driver to move cooperatively with the first carriage driver when both carriage drivers positively engage the engagement features on the corresponding instrument drivers and are thereby rotationally coupled. Contrary motion of the second carriage driver may include holding the second carriage driver stationary.

First Embodiment

If the first ISA coupler 330A is rotated by the corresponding carriage driver 320 that has been previously engaged with the first ISA coupler and the second ISA coupler 330B is held stationary by the corresponding carriage driver 320 that has been previously engaged with the second ISA coupler, friction will cause both instrument drivers 610 to either rotate or remain stationary depending on which set of instrument engagement features 630 creates a stronger frictional force. Both situations will ensure a proper engagement between the ISA engagement features 500 and the instrument engagement features 630 for both ISA couplers 330A, 330B.

In the first situation, the first ISA coupler 330A is rotated and causes both instrument drivers 610A, 610B to rotate. The second instrument driver 610B, which is rotating, will eventually engage the second ISA coupler 330B, which is being held stationary. It will be appreciated that occasionally the second instrument driver 610B will engage the second ISA coupler 330B without the need to rotate the first ISA coupler 330A.

Upon positive engagement of the second instrument driver 610B with the second ISA coupler 330B, both instrument drivers 610A, 610B will now be held stationary against the frictional force between the rotating first ISA coupler 330A and its corresponding first instrument driver 610A. The first ISA coupler 330A, which is rotating, will eventually engage the first instrument driver 610A, which is being held stationary. Thus both instrument drivers 610 will be positively engaged with their corresponding ISA couplers.

In the second situation, the second ISA coupler 330B is held stationary and causes both instrument drivers 610A, 610B to remain stationary. The first ISA coupler 330A, which is rotating, will eventually engage the first instrument driver 610A, which is being held stationary. It will be appreciated that occasionally the first instrument driver 610A will engage the first ISA coupler 330A without the need to rotate the first instrument driver.

Upon positive engagement of the first instrument driver 610A with the first ISA coupler 330A, both instrument drivers 610A, 610B will now be rotated against the frictional force between the stationary second ISA coupler 330B and its corresponding second instrument driver 610B. The second ISA coupler 330B, which is being held stationary, will eventually engage the second instrument driver 610B, which is rotating. Thus both instrument drivers 610 will be positively engaged with their corresponding ISA couplers.

Therefore, by keeping either the first ISA coupler 330A or the second ISA coupler 330B stationary while rotating the other, the rotationally coupled instrument drivers 610 are ensured to successfully engage with the corresponding ISA couplers 330 despite the absence of a hard-stop for the instrument drivers. It will be appreciated that the frictional engagement between the instrument drivers and the ISA couplers may be such that both the first and second situations occur alternately before positive engagement of one of the instrument drivers with its corresponding ISA coupler occurs.

Second Embodiment

In a second embodiment, in order to ensure that the friction caused by the ISA engagement features 500 coming in contact with the instrument driver disks 610 of a surgical instrument 120 does not prevent a proper engagement between the ISA engagement features 500 and the instrument engagement features 630, the first and second ISA couplers 330A, 330B are rotated simultaneously in opposite directions. In doing so, the friction created will cause both instrument drivers 610 to either rotate or remain stationary allowing the ISA couplers 330 to align with the instrument drivers 610 and properly engage.

For example, still referring to FIG. 8, by rotating the first ISA coupler 330A clockwise and rotating the second ISA coupler 330B counterclockwise with the corresponding carriage drivers 320 that have been previously engaged with the ISA couplers, friction between the engagement features and the disk surfaces will cause the rotationally coupled instrument drivers 610 to rotate in the same direction as one of the ISA couplers and in the opposite direction from the other ISA coupler. The ISA coupler that is rotating in the opposite direction from its corresponding instrument driver will eventually engage the corresponding instrument driver. It will be appreciated that occasionally one of the instrument drivers 610 will engage the corresponding ISA coupler 330 without the need to rotate the ISA couplers 330.

Upon positive engagement of the oppositely rotating instrument driver 610 with the corresponding ISA coupler 330, both instrument drivers 610 will now rotate in the opposite direction against the frictional force between the unengaged rotating ISA coupler and its corresponding instrument driver. The unengaged ISA coupler 330, which is now rotating in the opposite direction from the instrument drivers 610, will eventually engage the unengaged instrument driver. Thus both instrument drivers 610 will be positively engaged with their corresponding ISA couplers. Rotating the ISA couplers 330 in opposite directions ensures that the instrument drivers 610 will successfully engage with the corresponding ISA coupler 330.

In some embodiments, the positive engagement of both instrument drivers 610 with their corresponding ISA couplers 330 is detected. Detection of the positive engagement of both instrument drivers may cause the carriage drivers to stop driving the ISA couplers with the rotations used for engaging the instrument drivers. Positive engagement of an instrument driver may be detected by detecting axial movement of a spring loaded component as the engagement features move into the their engaged positions. Positive engagement of an instrument driver may also be detected by changes in the electrical characteristics of the motors that drive the carriage drivers, such as an increased current demand because of an increased load on the motor.

In the embodiment and figures discussed above, only two instrument drivers 610 have been illustrated as being coupled through one or more gears to an instrument shaft coupler 620. This should not be construed as limiting, but instead, the number of instrument drivers 610 coupled through one or more gears to an instrument shaft coupler 620 is variable dependent on the configuration of the surgical instrument 120. Furthermore, other embodiments may include two or more instrument drivers 610 directly coupled to each other through one or more gears. This coupling of instrument drivers 610 may also be coupled to an instrument shaft coupler 620 through one or more gears.

Furthermore, as is seen in the figures provided, it is not necessary for the pockets to be located on the instrument drivers 610 and the bosses to be located on the ISA couplers 330. Instead, one embodiment may include the instrument drivers 610 including bosses and the ISA couplers 330 including pockets.

It will also be recognized that the ISA couplers 330 serve to extend the corresponding carriage drivers 320 and provide a disposable, sterile covering for the carriage and carriage drivers. If the disposable, sterile covering of the ISA 300 is not needed, the method of engaging the ISA couplers 330 with the instrument drivers 610 may be applied to directly engaging the carriage drivers 320 with the instrument drivers.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. A teleoperated system comprising:
   an instrument including a first instrument driver and a second instrument driver rotationally coupled to each other;
   an instrument manipulator including a first carriage driver and a second carriage driver, wherein each of the first and second carriage drivers is configured to be able to rotate independently of the other of the first and second carriage drivers, wherein each of the first and second carriage drivers includes a first engagement feature, wherein the first carriage driver is configured to couple to and transfer rotation to the first instrument driver, and wherein the second carriage driver is configured to couple to and transfer rotation to the second instrument driver; and
   a manipulator controller configured to:
      control rotation of each of the first carriage driver and the second carriage driver; and
      control a motion of the second carriage driver to be contrary to the rotation of the first carriage driver until the first engagement feature of the first carriage driver positively engages a second engagement feature of the first instrument driver and the first engagement feature of the second carriage driver positively engages a second engagement feature of the second instrument driver, wherein the manipulator controller is configured to control the motion of the second carriage driver to be contrary to the rotation of the first carriage driver by holding the second carriage driver rotationally stationary or by rotating the second carriage driver opposite to the rotation of the first carriage driver.

2. The teleoperated system of claim 1, wherein the manipulator controller is configured to control the motion of the second carriage driver to be contrary to the rotation of the first carriage driver by:
   rotating the first carriage driver and holding the second carriage driver stationary until the first engagement feature of the first carriage driver positively engages the second engagement feature of the first instrument driver and the first engagement feature of the second carriage driver positively engages the second engagement feature of the second instrument driver.

3. The teleoperated system of claim 1, wherein the manipulator controller is configured to control the motion of the second carriage driver to be contrary to the rotation of the first carriage driver by:
   rotating the first carriage driver and the second carriage driver such that the first instrument driver is rotating in a direction opposite to the rotation of the first carriage driver, or the second instrument driver is rotating in a direction opposite to the rotation of the second carriage driver, until the first engagement feature of the first carriage driver positively engages the second engagement feature of the first instrument driver and the first engagement feature of the second carriage driver positively engages the second engagement feature of the second instrument driver.

4. The teleoperated system of claim 1, wherein each of the first carriage driver and the second carriage driver is caused to move axially by a spring force to frictionally couple the rotation of the first carriage driver to the first instrument driver and the rotation of the second carriage driver to the second instrument driver.

5. The teleoperated system of claim 4, wherein the manipulator controller is further configured to detect positive engagement of the first engagement feature of the first carriage driver with the second engagement feature of the first instrument driver and the first engagement feature of the second carriage driver with the second engagement feature of the second instrument driver by detecting axial movement of the first carriage driver and the second carriage driver.

6. The teleoperated system of claim 1, further comprising a first electric motor coupled to the first carriage driver and a second electric motor coupled to the second carriage driver.

7. The teleoperated system of claim 1, wherein each first engagement feature of the first and second carriage drivers comprises a pocket, and wherein each second engagement feature of the first and second instrument drivers comprises a boss.

8. The teleoperated system of claim 1, wherein each first engagement feature of the first and second carriage drivers comprises a boss, and wherein each second engagement feature of the first and second instrument drivers comprises a pocket.

9. The teleoperated system of claim 1, further comprising the instrument, wherein the first instrument driver is rotationally coupled to the second instrument driver by gears.

10. The teleoperated system of claim 1, further comprising the instrument, wherein the instrument further includes an instrument shaft that can be rotated indefinitely, and wherein the first instrument driver and the second instrument driver of the instrument are rotationally coupled to each another by being rotationally coupled to the instrument shaft.

11. The teleoperated system of claim 10, wherein the first instrument driver and the second instrument driver are each rotationally coupled to the instrument shaft directly by gears.

12. The teleoperated system of claim 1, wherein controlling the motion of the second carriage driver further comprises using at least one electric motor, and wherein the manipulator controller is further configured to detect the positive engagement by: detecting changes in electric characteristics of the at least one electric motor.

13. A method of coupling an instrument with an instrument manipulator, wherein the instrument manipulator is supporting the instrument, wherein the instrument includes a first instrument driver and a second instrument driver, and wherein the first instrument driver and the second instrument driver are rotationally coupled to each other, the method comprising:

controlling a rotation of each of a first carriage driver and a second carriage driver of the instrument manipulator, wherein the first carriage driver is configured to be independently rotatable relative to the second carriage driver and the second carriage driver is configured to be independently rotatable relative to the first carriage driver, wherein each of the first and second carriage drivers includes a first engagement feature, wherein the first carriage driver is configured to couple to and transfer rotation to the first instrument driver, and wherein the second carriage driver is configured to couple to and transfer rotation to the second instrument driver; and imparting a motion to the second carriage driver that is contrary to the rotation of the first carriage driver until the first engagement feature of the first carriage driver positively engages a second engagement feature of the first instrument driver and the first engagement feature of the second carriage driver positively engages a second engagement feature of the second instrument driver, wherein imparting the motion to the second carriage driver that is contrary to the rotation of the first carriage driver includes: holding the second carriage driver rotationally stationary or rotating the second carriage driver opposite to the rotation of the first carriage driver.

14. The method of claim 13, wherein imparting the motion to the second carriage driver that is contrary to the rotation of the first carriage driver further comprises:

rotating the first carriage driver and holding the second carriage driver stationary until the first engagement feature of the first carriage driver positively engages the second engagement feature of the first instrument driver and the first engagement feature of the second carriage driver positively engages the second engagement feature of the second instrument driver.

15. The method of claim 13, wherein imparting the motion to the second carriage driver that is contrary to the rotation of the first carriage driver further comprises:

rotating the first carriage driver and the second carriage driver such that the first instrument driver is rotating in a direction opposite to the rotation of the first carriage driver or the second instrument driver is rotating in a direction opposite to the rotation of the second carriage driver until the first engagement feature of the first carriage driver positively engages the second engagement feature of the first instrument driver and the second carriage driver positively engages the second engagement feature of the second instrument driver.

16. The method of claim 13, further comprising:
axially displacing, by a spring force, the first carriage driver against the first instrument driver and the second carriage driver against the second instrument driver; and
frictionally coupling, by the spring force, the first carriage driver to the first instrument driver and the second carriage driver to the second instrument driver.

17. The method of claim 13, further comprising:
positively coupling the first carriage driver to a first instrument sterile adapter coupler and the second carriage driver to a second instrument sterile adapter coupler; and
positively coupling the first instrument sterile adapter coupler to the first instrument driver and the second instrument sterile adapter coupler to the second instrument driver.

18. The method of claim 13, further comprising:
controlling, by a manipulator controller, the rotation of each of the first carriage driver and the second carriage driver; and
controlling, by the manipulator controller, the motion of the second carriage driver that is contrary to the rotation of the first carriage driver.

19. The method of claim 18, further comprising detecting, by the manipulator controller, positive engagement of the first engagement feature of the first carriage driver with the second engagement feature of the first instrument driver and the first engagement feature of the second carriage driver with the second engagement feature of the second instrument driver.

20. The method of claim 19, further comprising:
detecting, by the manipulator controller, axial movement of each of the first carriage driver and the second carriage driver; and
determining, by the manipulator controller and based on the detected axial movement of the first carriage driver and the second carriage driver, positive engagement of the first engagement feature of the first carriage driver and the second engagement feature of the first instrument driver and the first engagement feature of the second carriage driver and the second engagement feature of the second instrument driver.

21. The method of claim 19, wherein imparting the motion to the second carriage driver further comprises using at least one electric motor, and wherein detecting the positive engagement of the first engagement feature of the first carriage driver and the second engagement feature of the first instrument driver and the first engagement feature of the second carriage driver and the second engagement feature of the second instrument driver comprises: detecting changes in electric characteristics of the at least one electric motor.

* * * * *